United States Patent
Johnson et al.

(10) Patent No.: US 7,176,325 B2
(45) Date of Patent: Feb. 13, 2007

(54) SELECTIVE ACYLATION OF SECONDARY HYDROXYL GROUPS

(75) Inventors: James H. Johnson, Merrimac, MA (US); Richard J. Pariza, Zion, IL (US); Rex T. Gallagher, Beverly, MA (US)

(73) Assignee: Natural Pharmaceuticals, Inc., Beverly, MA (US)

( * ) Notice: Subject to any disclaimer, the term of this patent is extended or adjusted under 35 U.S.C. 154(b) by 0 days.

(21) Appl. No.: 10/510,063

(22) PCT Filed: Apr. 5, 2003

(86) PCT No.: PCT/US03/10556

§ 371 (c)(1),
(2), (4) Date: Oct. 4, 2004

(87) PCT Pub. No.: WO03/087078

PCT Pub. Date: Oct. 23, 2003

(65) Prior Publication Data

US 2005/0176975 A1 Aug. 11, 2005

Related U.S. Application Data

(60) Provisional application No. 60/370,252, filed on Apr. 5, 2002.

(51) Int. Cl.
*C07D 305/00* (2006.01)
*C07D 407/00* (2006.01)
*C07D 493/00* (2006.01)

(52) U.S. Cl. ...................................... 549/510; 549/511
(58) Field of Classification Search ............... 549/510, 549/511
See application file for complete search history.

(56) References Cited

U.S. PATENT DOCUMENTS

| 3,598,806 A | 8/1971 | Morozowich |
| 4,942,184 A | 7/1990 | Haugwitz et al. |
| 5,319,112 A | 6/1994 | Kingston et al. |
| 5,411,984 A * | 5/1995 | Kingston et al. ............ 514/449 |

FOREIGN PATENT DOCUMENTS

| EP | 0 639 577 A1 | 2/1995 |
| GB | 2 289 277 A | 11/1995 |
| JP | 2000117115 | 4/2000 |
| WO | WO 95/11020 | 4/1995 |

OTHER PUBLICATIONS

Yamaguchi et al., "Synthesis of Taxoids 5. Synthesis and Evaluation of novel water-soluble prodrugs of a 3'-desphenyl-3'-cyclopropyl analogue of decetaxel", Bioorganic & medicinal chemistry letters, vol. 9, pp. 1639-1644.*

Groot et al., "Synthesis and biological evaluation of 2'-carbamate-linked and 2'-carbonate-linked prodrugs of paclitaxel: selective activation by the tumor-associated protease plasmin", J. Med. Chem., vol. 43, pp. 3093-3102.*

Greenwald et al., "Highly water soluble taxol derivatives: 7-polyethylene glycol carbamates and carbonates", J. Org. Chem., vol. 60, pp. 331-336.*

Golik et al. "Synthesis and antitumor evaluation of paclitaxel phosphonooxymethyl ehters: a novel class of water soluble paclitaxel pro-drugs", Bioorganic & medicinal chemistry letters, vol. 6, pp. 1837-1842.*

Jae Wook Lee, June Y. Lu, P. S. Low and P. L. Fuchs; Synthesis and Evaluation of Taxol-Folic Acid Conjugates as Targeted Antineoplastics; Bioorganic & Medicinal Chemistry; vol. 10; 2002; pp. 2397-2414 (XP-002368067).

Richard B. Greenwald, Annapurna Pendri and Durgadas Bolikal; Highly Water Soluble Taxol Derivatives: 7-Polyethylene Glycol Carbamates and Carbonates; J. Org. Chem.; vol. 60; 1995; pp. 331-336 (XP-001037523).

Supplementary European Search Report for European Patent Application No. 03 72 8345 dated Feb. 16, 2006.

* cited by examiner

*Primary Examiner*—Margaret D. Seaman
*Assistant Examiner*—Niloofar Rahmani
(74) *Attorney, Agent, or Firm*—Alston & Bird LLP

(57) ABSTRACT

The invention provides methods and compositions for selectively acylating a specific hydroxyl group in a molecule of interest containing at least two unprotected secondary hydroxyl groups. Although the methods and compositions of the invention have general applicability, they are particularly useful in the selective acylation of taxane molecules.

43 Claims, No Drawings

SELECTIVE ACYLATION OF SECONDARY HYDROXYL GROUPS

CROSS REFERENCE TO RELATED APPLICATIONS

The application claims priority from U.S. Provisional application Ser. No. 60/370,252, filed Apr. 5, 2002. This application is incorporated herein by reference in its entirety.

FIELD OF THE INVENTION

The invention relates generally to methods and compositions for selectively acylating a secondary hydroxyl group of a compound comprising a plurality of unprotected secondary hydroxyl groups. More specifically, the invention relates to methods and compositions for selectively acylating the C-2' hydroxyl group of a taxane molecule containing an unprotected C-7 hydroxyl group.

BACKGROUND OF THE INVENTION

Acylation is a process frequently used in the chemical arts to introduce one or more carbonyl-containing substituents into a compound of interest, often to protect hydroxyl or amine groups. Over the years, investigators have identified a variety of reagents and reaction conditions for acylating particular functionalities. Of particular interest is the ability to selectively acylate a desired functionality without the need to protect and deprotect other reactive sites thereby creating a more efficient synthetic scheme.

For example, Ishihara et al. describe a method for selectively acylating a primary alcohol in presence of secondary alcohols using an acyl chloride (Ishihara et al. (1993) *J. Org. Chem.* 58: 3791-3793). In an exemplary reaction scheme, a 1:1 mixture of 1-octanol and 2-octanol in methylene chloride was reacted with acetyl chloride in the presence of various bases, for example, 2,4,6-collidine, N,N-diisopropylethylamine, or 1,2,2;6,6-pentamethylpiperidine. Under the conditions described, the primary alcohol in 1-octanol was acylated preferentially over the secondary alcohol in 2-octanol.

Garegg et al. similarly describe the regioselective acetylation of the primary alcohols of a tetrasaccharide in the presence of its secondary alcohols (Garegg (1997) *J. Carbohydr. Chem.* 16(7): 973–981). Specifically, Garegg et al. utilize an excess of acetyl chloride and collidine in methylene chloride at low temperature (−70° C.) to perform the selective acetylation.

In another example, Szeja identified reaction conditions to selectively acylate a secondary hydroxyl group at either the 2-position or the 3-position in a sugar molecule where both hydroxyl groups are initially unprotected (Szeja (1979) *Synthesis* 821–822). In the paper, Szeja reports that methyl 4,6-O-benzlidene-a-D-galactopyranoside was partially esterified in 46% yield at its more reactive 3-hydroxyl group using benzoyl chloride and pyridine (see, e.g., Haines (1976) *Adv. Carbohydr. Chem. Biochem.* 33: 11). However, Szeja discloses the regioselective benzoylation of methyl 4,6-O-benzlidene-a-D-galactopyranoside at either its 2-hydroxyl group or its 3-hydroxyl group via phase transfer catalysis. More specifically, when benzoyl chloride was added to methyl 4,6-O-benzlidene-a-D-galactopyranoside in benzene and hexamethylphosphoric triamide with tetrabutylammonium chloride and a 40% aqueous sodium hydroxide solution forming the aqueous phase, the reaction provided the 3-O-benzoyl product in a 62% yield. In contrast, when benzoyl chloride was added to methyl 4,6-O-benzlidene-a-D-galactopyranoside in the same phase transfer catalysis system without the hexamethylphosphoric triamide present, the reaction provided the 2-O-benzoyl product in a 69% yield.

Regarding the acylation of taxanes, U.S. Pat. Nos. 5,319,112 and 5,470,866 describe reaction conditions for acylating the hydroxyl groups at the C-2' positions of the taxane molecules paclitaxel and dihydrocephalomannine. In the reactions, a mixture of paclitaxel and dihydrocephalomannine dissolved in acetonitrile was combined with benzoic acid, dicyclohexylcarbodiimide and 4-(N,N-dimethylamino)pyridine. The reaction resulted in benzoylation of the C-2' position of paclitaxel and dihydrocephalomannine. Taxane molecules acylated at the C-2' position reportedly are useful starting materials for producing oxalate and oxamido derivatives of taxanes (se U.S. Pat. No. 5,470,866).

Paclitaxel, also known as taxol A (TAXOL® being a registered trademark of the Bristol-Myers Squibb Company), is a member of the taxane family, and is a naturally occurring diterpenoid. Paclitaxel has been shown to have great value as an anti-cancer drug. Paclitaxel can be isolated from certain yew trees, for example, *Taxus brevifolia*, and certain species of *Taxus media* (e.g., species known as "Hill," "Hicksii" and "dark green spreader") (see U.S. Pat. No. 5,744,333), extracted from cell cultures, or synthesized completely or partially in vitro. Notwithstanding these methods, the global supply of paclitaxel has been quite limited, and there is an ongoing need for other methods for producing paclitaxel cost effectively on a larger scale.

Because of the promising clinical activity of certain taxanes (e.g., paclitaxel) against various types of cancer, there is an ongoing need for different methods for preparing paclitaxel and other taxane molecules, including paclitaxel derivatives and analogues. There also is a need for paclitaxel derivatives having a range of in vivo and in vitro activities, as well as paclitaxel derivatives having similar biological activities to paclitaxel. It is believed that the preparation of paclitaxel analogues may result in the synthesis of compounds with comparable or greater potency, superior bioavailability, or fewer side effects than paclitaxel. In support of this approach, a paclitaxel analogue known as docetaxel (TAXOTERE®) has been identified.

Docetaxel, which differs from paclitaxel only in the nature of the N-acyl substituent and the absence of a 10-acetyl group, is reported to be twice as active as paclitaxel in certain assays (see U.S. Pat. No. 5,319,112). It is contemplated that other paclitaxel derivatives not yet identified may have other beneficial and pharmacologically desirable properties. Furthermore, there is also need for paclitaxel analogues that can be used as taxane standards. For example, it is desirable to make easily synthesizable analogues that can be used for characterizing structure-activity relationships of taxane molecules, as chromatography standards, or starting or intermediate molecules in the synthesis of various other taxane molecules.

SUMMARY OF THE INVENTION

It is an object of the invention to provide methods and compositions for selectively acylating a secondary hydroxyl group of interest in a compound that contains a plurality of unprotected secondary hydroxyl groups using an acid halide and a hindered base. Although the invention described herein has general applicability in the chemical arts, it has particular applicability in the synthesis of taxane molecules.

In one aspect, the invention provides a method for selectively acylating a compound comprising at least two secondary hydroxyl groups that are unprotected. The method generally comprises the steps of providing a solution of the compound of interest in a suitable solvent and contacting the solution with a base (e.g., hindered base) and an acylating agent (e.g., acid halide) thereby to selectively acylate one secondary hydroxyl group relative to at least one other secondary hydroxyl group. Alternatively, the acylating agent may be a carboxylic acid anhydride or a carboxylic acid in conjunction with a coupling agent such as dicyclohexylcarbodiimide or N-(3-dimethylaminopropyl)-N'-ethylcarbodiimide. Other hydroxyl acylating agents known in the art may also be used in the present invention. A list of these alternatives is described in J. W. Barton, "Protecting Groups in Organic Chemistry," J. G. W. McOmie, ed., Plenum Press, New York, N.Y., 1973, and in T. W. Greene and P. G. M. Wuts, "Protective Groups in Organic Synthesis," John Wiley & Sons, New York, N.Y., 1999. In the present invention, the compound to be acylated may be any molecule that comprises at least two secondary hydroxyl groups. In a preferred embodiment, such compound is a taxane molecule.

In a preferred embodiment, the acid halide is an acid chloride and the hindered base is a trialkylamine or a pyridine derivative. Preferred acid chlorides include benxoyl chloride, tigloyl chloride, hexanoyl chloride, butyryl chloride, 2-methylbutyryl chloride, phenylacetyl chloride, furoyl chloride, and tert-butyl chloroformate. Preferred trialkylamines include N-ethyldicyclohexylamine, NN-diisopropylethylamine, and tripropylamine. Preferred pyridine derivatives include 2,6-lutidine, 2,4,6-collidine, 2,3,5,6-tetramethylpyridine, 2,6-di-tert-butylpyridine, and 2,6-di-tert-butyl-4-(dimethylamino) pyridine or 2,6-dimethyl-4 (dimethylamino)pyridine.

In preferred embodiments of the above-described methodology, the invention provides a method of selectively acylating a hydroxyl group located at the C-2' position of a taxane molecule while the hydroxyl group located at the C-7 position of the taxane molecule is unprotected. The method comprises the steps of providing a solution comprising a taxane molecule in an organic solvent and contacting the solution with a hindered base and an acid halide thereby to acylate the hydroxyl group located at the C-2' position of the taxane molecule. The acid halides and hindered bases described above are applicable to this preferred embodiment.

The selective acylation process preferably occurs within six hours, or more preferably within four hours, after addition of the acid halide and the hindered base to a compound of interest. Additionally, the selective acylation reaction preferably occurs at a temperature of about 40° C. or less, or more preferably at about ambient temperature, e.g., from about 20° C. to about 25° C.

The organic solvent used in the selective acylation reaction of a taxane molecule typically is an aprotic solvent that solubilizes a taxane molecule at a concentration of at least about 10% by weight, and preferably at least about 15% by weight Tetrahydrofuran is the Preferred Organic Solvent The foregoing, and other features and advantages of the invention, as well as the invention itself, will be more fully understood from the description, figures, and claims which follow.

DETAILED DESCRIPTION OF THE INVENTION

It has been discovered that a secondary hydroxyl group can be selectively acylated in the presence of other unprotected secondary hydroxyl groups using an acid halide and a hindered base. The methods of the invention may permit selective acylation to occur in a relatively short time and/or under relatively mild reaction conditions. By exploiting methods of the invention, it is possible to eliminate protection/deprotection steps in the overall synthetic sequence of a target compound, e.g., a biologically active natural product. In particular, the method of the invention has utility in the synthesis and/or transformation of taxane molecules.

As used herein, an "acid halide" is a compound which contains a carboxy halide functionality, i.e., —C(O)X, where X is a halogen such as fluorine, chlorine, bromine, or iodine. An acid halide can include an alkoxy group, an alkyl group, an aryl group, an arylalkyl group, an ester group, an ether group, a heterocyclic group, a vinyl group, and combinations thereof. An acid halide also may be substituted with substituents such as alkanoyloxy groups, alkenyl groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred acid halides are acid chlorides such as benzoyl chloride, tigloyl chloride, hexanoyl chloride (caproyl chloride), butyryl chloride, 2-methylbutyryl chloride, phenylacetyl chloride, furoyl chloride, and tert-butyl chloroformate.

As used herein, an "acyl group" means a linear, branched, or cyclic substituent having a carbonyl group which is attached to either an oxygen atom, e.g., of a hydroxyl group, or a nitrogen atom, e.g., of an amino group. An acyl group can include an alkoxy group, an alkyl group, an aryl group, an arylalkyl group, an ester group, an ether group a heterocyclic group, a vinyl group, and combinations thereof. An acyl group also may be substituted with substituents such as alkanoyloxy groups, alkenyl groups, alkylsilyl groups, alkysulfonyl groups, alkylsulfoxy groups, alkylthio groups, alkynyl groups, amino groups such as mono- and di-alkylamino groups and mono- and di-arylamino groups, amide groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combination of these. It should be understood that an acyl group also can be an amino protecting group or a hydroxyl protecting group. As a hydroxyl protecting group, an acyl group may form an ester or carbonate. As an amino protecting group, an acyl group may form an amide or a carbamate. Examples of acyl groups include, but are not limited to, alkoyl groups, aroyl groups, arylalkoyl groups, vinoyl groups. Preferred acyl groups are benzoyl, ethanoyl, tigloyl, or 2-methyl-2-butenoyl, 2-methyl-1-propenoyl, hexanoyl, butyrl, 2-methybutyryl, phenylacetyl, propanoyl, furoyl, and tert-butyloxycarbonyl.

As used herein, an "acylating agent" includes any agent that when reacted with a hydroxyl group or amine group yields an ester carbonate amide or carbanate. Acylating agents may include, but are not limited to, a carboxylic acid anhydride or a carboxylic acid in conjunction with a coupling agent such as dicyclohexylcarbodiimide or N-(3-dimethylaminopropyl)-N'-ethylcarbodiimide. Other hydroxyl acylating agents known in the art may also be used in the present invention. A list of these alternatives is described in J. W. Barton, "Protecting Groups in Organic Chemistry," J. G. W. McOmie, ed., Plenum Press, New York, N.Y., 1973, and in T. W. Greene and P. G. M. Wuts, "Protective Groups in Organic Synthesis," John Wiley & Sons, New York, N.Y., 1999.

As used herein, an "alkoxy group" means a linear, branched, or cyclic saturated hydrocarbon attached to an oxygen atom. Preferably, an alkoxy group has between one and six carbon atoms. An alkoxy group also refers to substituted alkoxy groups, which may include substituents such as alkanoyloxy groups, alkenyl groups, alkyl groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred examples of alkoxy groups include, among others, methoxy, ethoxy, propoxy, cyclopropoxy, isopropoxy, n-butoxy, isobutoxy, sec-butoxy, tert-butoxy, cyclobutoxy, pentoxy, isopentoxy, neo-pentoxy, cyclopentoxy, hexoxy, and cyclohexoxy.

As used herein, an "alkyl group" means a linear, branched, or cyclic saturated hydrocarbon. Preferably, an alkyl group has between one and six carbon atoms. An alkoxy group also refers to substituted alkyl groups, which may include substituents such as alkanoyloxy groups, alkenyl groups, alkoxy groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, amino groups such as dialkylamino groups, diarylamino groups, carboxylic acid-containing groups, haloalkyl groups, halogens, hydroxyl groups, nitrile groups, nitro groups, and sulfonic acid groups. Examples of preferred alkyl groups include, but are not limited to, methyl, ethyl, propyl, isopropyl, cyclopropyl, n-butyl, isobutyl, sec-butyl, tert-butyl, cyclobutyl, pentyl, isopentyl, neo-pentyl, 1-ethylpropyl, cyclopentyl, hexyl, and cyclohexyl.

As used herein, an "amino protecting group" means a substituent of an amino group that is employed to block or protect the amino functionality, often while reacting other functional groups on the molecule. Example of amino protecting groups are well known in the art and are described in J. W. Barton, "Protecting Groups in Organic Chemistry," J. G. W. McOmie, ed., Plenum Press, New York, N.Y., 1973, and in T. W. Greene and P. G. M. Wuts, "Protective Groups in Organic Synthesis," John Wiley & Sons, New York, N.Y., 1999. It should be understood that an amino protecting group may remain on an end product.

As used herein, an "aryl group" means a phenyl group or naphthyl group, which is optionally substituted. Examples of substituents on aryl groups include, but are not limited to, alkanoyloxy groups, alkenyl groups, alkoxy groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, alkyl groups, amino groups such as dialkylamino groups, diarylamino groups, carboxylic acid-containing groups, haloalkyl groups, halogens, hydroxyl groups, nitrile groups, nitro groups, and sulfonic acid groups.

As used herein, an "arylalkyl group" means an aryl group attached to an alkyl group. An example of an arylalkyl group is a benzyl group.

As used herein, a "basic baccatin m structure" means a compound having the formula:

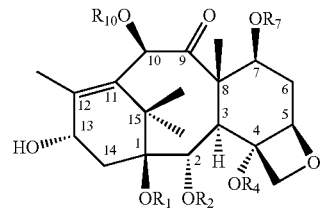

where each of $R_1$, $R_2$, $R_4$, $R_7$, and $R_{10}$ independently is hydrogen, an alkyl group, an acyl group, an aryl group, an arylalkyl group, a vinyl group, an ether group, an ester group, a glycoside group, an oxo-group, or a hydroxyl protecting group. Included within the definition of a basic baccatin III structure is baccatin III, which has the formula:

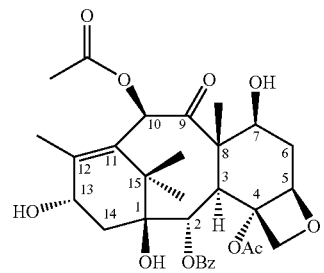

and 10-deacetylbaccatin III, which has the formula:

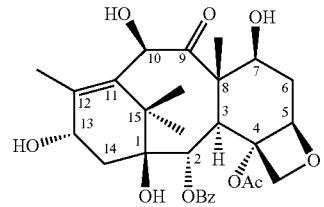

where Ac is an acetyl or acetate group ($CH_3C(O)$—), and Bz is a benzoyl group ($PhC(O)$— or $C_6H_5C(O)$—)

As used herein, an "ester group" means a linear, branched, or cyclic substituent having an ester functionality, i.e., —C(O)O—. Examples of ester groups include acyl groups such as ethanoyl and propanoyl, which are bound to a hydroxyl group.

As used herein, an "ether group" means a linear, branched, or cyclic substituent having an ether functionality, i.e., —COC—. An examples of an ether group includes, but are not limited to, $HOCH_2CH_2OC(CH_2OH)H$—.

As used herein, a "glycoside group" or a "glycosyl group" means any of a number of sugar derivatives that contain a non-sugar group bonded to an oxygen or nitrogen atom and that on hydrolysis yield a sugar such as glucose. An example of a preferred gylcosyl group is xylosyl.

As used herein, a "halogen" means fluorine, chlorine, bromine, and/or iodide.

As used herein, a "heterocyclic group" is a saturated, unsaturated, or aromatic cyclic compound that contains at least one atom other than carbon, e.g., oxygen, nitrogen, or sulfur, in a ring. Examples of heterocyclic groups include furyls such as 2-furan, morpholino, piperidino, piperazino, N-methylpiperazino, pyrrollyl, pyridyl, and thiophene.

As used herein, the term "hindered base" includes any base that has a three-dimensional structure or contains one or more substituents which prevents the base or a reactive intermediate thereof from reacting with at least one of at least two unprotected secondary hydroxyl groups present in a molecule. In one alternative embodiment, the hindered base is a trialkylamine where at least one of the alkyl groups is larger than ethyl, or a pyridine derivative that is substituted at least at its 2-position, e.g. 2-ethylpyridine. Preferably, the hindered base is a trialkylamine having two of its alkyl groups larger than ethyl, or a pyridine derivative that is substituted at least at its 2- and 6-positions include, but are not limited to, alkyl groups, alkoxy groups, and halogens. Examples of hindered bases include, but are not limited to, 2,3,5-collidine, 2,4,6-collidine, 2,6-di-tert-butylpyridine, 2-6-di-tert-butl -4-(dimethylamino)pyridine, 2,6 di-methyl-4-(dimethylamino)pyridine, 2,3-lutidine, 2,4-lutidine, 2,5-lutidine, 2,6-lutidine, 2,3,5,6-tetramethylpyridine, N-tert-butylmorpholine, N,N-diisopropylethylamine, N,N-diisopropylisobutylamine, N-ethyldicyclohexylamine, triethylamine, triisoproplyamine, tripropylamine, imidazole, 1,5-diazabicylo[4.3.0]non-5-ene (DBN), 1,4-diazabicylo[2.2.2.]octane (Dabco™), 1,8-diazabicylo[5.4.0]undec-7-ene (DBI).

As used herein, a "hydroxyl protecting group" means a substituent of a hydroxyl group that is employed to block or protect the hydroxyl functionality, often while reacting other functional groups on the molecule. Examples of hydroxyl protecting groups are well known in the art and are described in J. W. Barton, "Protecting Groups in Organic Chemistry," J. G. W. McOmie, ed., Plenum Press, New York, N.Y., 1973, and in T. W. Green and P. G. M. Wuts, "Protective Groups in Organic Synthesis," John Wiley & Sons, New York, N.Y., 1999. It should be understood that a hydroxyl protecting group may remain on an end product. Examples of preferred hydroxyl protecting groups include, among others, acyl groups such as acetate (Ac) and benzoyl (Bz), trimethylsilyl (TMS), triethylsilyl (TES), trichloroethoxycarbonyl, 2,2,2-trichloroethyloxycarbonyl ($Cl_3CH_2OC(O)$—).

As used herein, an "oxo-group" means a substituent derived from the oxidation of a glycoside group such as a xyloside as described in U.S. Pat. No. 5,356,928.

As used herein, each of "selective acylation," "selectively acylating," and "selectively acylated" means that about 85% or greater of the end products is acylated at the desired secondary hydroxyl groups(s) without acylation of at least one other secondary hydroxyl group, regardless of the overall yield of the reaction. Preferably, about 90% or greater of the end products is acylated at the desired secondary hydroxyl group and/or about 5% or less of a bis- or higher order acylated product is formed and/or about 1% or less of the starting animal, i.e., the compound to be selectively acylated, remains unreacted. More preferably, about 95% or greater of the end products is acylated at the desired secondary hydroxyl group and/or about 2% or less of a bis- or higher order acylated product is formed and/or about 0.1% or less of the starting material remains unreacted.

As used herein, "taxane molecule" means a molecule that contains a basic baccatin III structure with a (2R,3S)—$C_6H_5CH(Rx)CH(OH)C(O)$— group forming an ester with the hydroxyl group located at the C-13 position of the basic baccatin III structure (where the reference numerals used to designate atom positions on a taxane molecule are in accordance with standard taxane nomenclature). The group represented by Rx can be an amino group, a salt of an amino group (e.g., an ammonium salt), an amino group which is protected with an amino protecting group, or a substituent which may be converted into an amino group. Various isomers, homologues, and analogues of the basic baccatin III structure, and of the (2R,3S)—$C_6H_5CH(Rx)CH(OH)C(O)$— group also are included within the definition of a taxane molecule. For example, a 10-deacetylbaccatin III structure is contemplated within the scope of a taxane molecule. Included within the definition of a taxane molecule are taxol A (paclitaxel), taxol B (cephalomannine), taxol C, taxol D, taxol E, taxol F, taxol G, docetaxel (TAXOTERE®), and nonataxel (see, e.g., Table 1).

As used herein, a "vinyl group" means a linear or branched substituent having a carbon-carbon double bond. Examples of vinyl groups include, but are not limited to, 1-methyl-1-propenyl ($CH_3CH=C(CH_3)$—) and 2-methyl-1-propenyl (($CH_3)_2C=CH$—).

TABLE 1

Examples of $R_N$ Groups In Known Taxane Molecules

| Taxane | $R_N$— | Molecular Structure |
|---|---|---|
| taxol A (paclitaxel) | phenyl | (structure) |

TABLE 1-continued

Examples of $R_N$ Groups In Known Taxane Molecules

| Taxane | $R_N-$ | Molecular Structure |
|---|---|---|
| taxol B (cephalomannine) | | 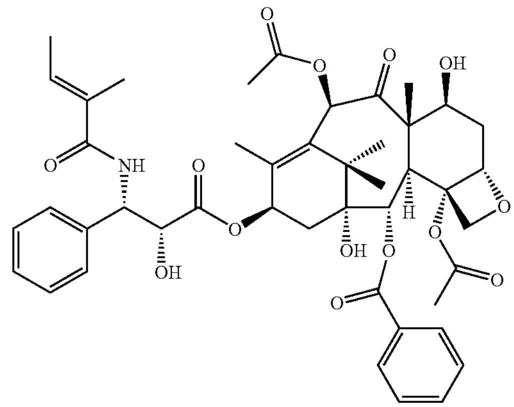 |
| taxol C | | 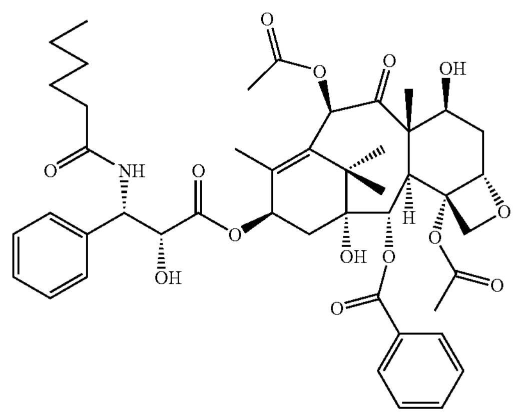 |
| taxol D | | 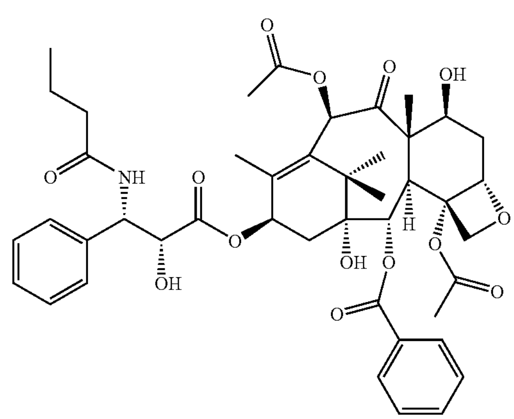 |

TABLE 1-continued

Examples of R_N Groups In Known Taxane Molecules

| Taxane | R_N— | Molecular Structure |
|---|---|---|
| taxol E | | 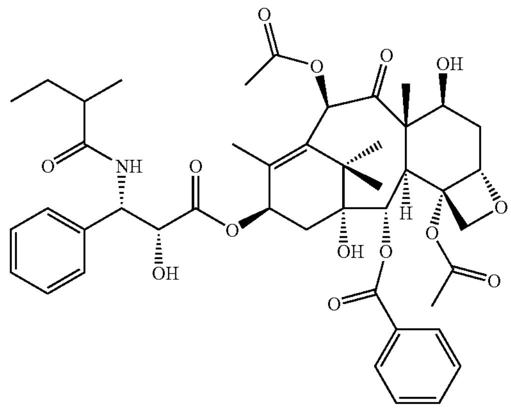 |
| taxol F | | 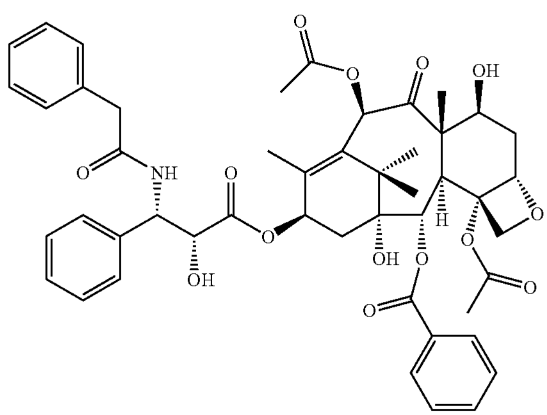 |
| taxol G | | 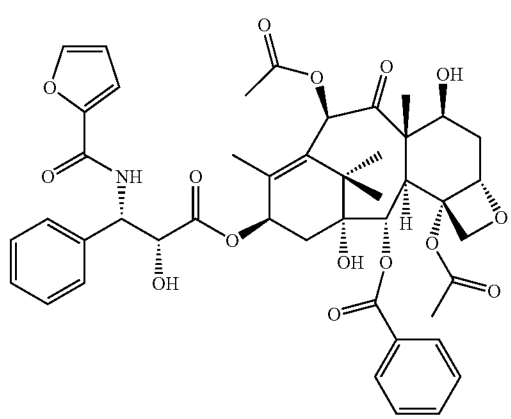 |

TABLE 1-continued

Examples of R_N Groups In Known Taxane Molecules

| Taxane | R_N— | Molecular Structure |
|---|---|---|
| Docetaxel (Taxotere ®) | 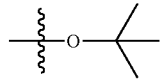 | 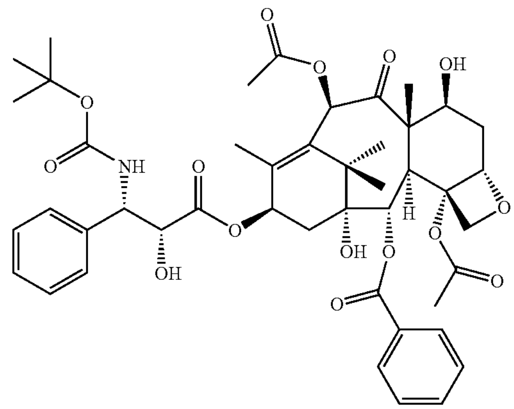 |
| Nonataxel | 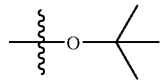 | 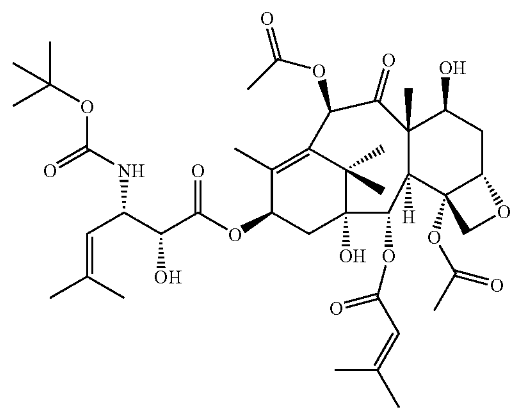 |

In the present invention, the taxane compound acylated in accordance with the present invention may be derived from any *Taxus* species, including but not limited to, *Taxus brevifolia*, *T. baccata* (European yew), *T. cuspidata*, *T. globosa* (Mexican yew), *T. floridana* (Florida yew), *T. canadenisis* (Canadian yew), *T. wallichiana* (Himalayan yew), *T. yunnanensis*, *T. chinensis*, and also a number of ornamental hybrids, such as *T.x media* cultivars, e.g.: *T.x media* 'Densiformis', *T.x* 'Hicksii', *T.x* 'Brownii', *T.x* 'Dark Green Spreader', *T.x* 'Runyan', *T.x* 'Wardii', *T.x* 'Tautonii', *T. cuspidata* 'Capitata', etc. Among *Taxus* species, *Taxus x media* cultivars are particularly preferred. For example, preferred cultivars include, but are not limited to, *T.x* 'Hicksii' or *T.x* 'Dark Green Spreader'. Further, the starting taxane compound may be derived from grown plant cells, or culture supernatants obtained by using in vitro culture technology. The starting taxane compound may also be obtained from semi-synthesis or total synthesis procedures.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

It should be understood that in addition to acid halide, a hindered base and one solvent, a selective acylation reaction of the invention may employ additional reagents including additional hindered or unhindered bases, additional solvents and/or solvent systems, and/or other chemicals and reagents not affecting the selective acylation reaction.

In one aspect, the invention relates to a method of selectively acylating a compound that contains at least two unprotected secondary hydroxyl groups using an acid halide and a hindered base. The method generally includes the steps of providing a solution of the compound in a solvent and contacting the solution with a hindered base and an acid halide whereby at least one secondary hydroxyl group is selectively acylated in preference to another secondary hydroxyl group.

Various acid halides may be used in the practice of the invention, e.g. acid fluorides, acid chlorides, acid bromides, and acid iodides. Depending on the particular end product and/or any reaction condition constraints, e.g., a temperature sensitive molecule, choice of a suitable acid halide is well within the skill of the art. Preferred acid halides include, among others, benzoyl halide, tigloyl halide, hexanoyl halide (caproyl halide), butyryl halide, 2-methylbutyryl halide, phenylacetyl halide, furoyl halide, and tert-butyl haloformate. However, acid chlorides are preferred.

Various hindered bases may be used in the practice of the invention, although trialkylamines and pyridine derivatives are preferred. As with the choice of an acid halide, a skilled artisan, with the knowledge of the invention, readily would be able to identify a particular hindered base suitable for the selective acylation of a specific molecule. In particular, the choice of hindered base depends on the spacial location and steric environment of the secondary hydroxyl groups of the starting material. Hindered bases include, but are not limited to, 2,3,5-collidine, 2,4,6-collidine, 2,6-di-tert-butylpyridine, 2-6-di-tert-butl-4-(dimethylamino)pyridine, 2,6-dimethyl-4-(dimethylamino)pyridine, 2,3-lutidine, 2,4-lutidine, 2,5-lutidine, 2,6-lutidine, 2,3,5,6-tetramethylpyridine, N-tert-butylmorpholine, N,N-diisopropylethylamine, N,N-diisopropylisoutylamine, N-ethyldicyclohexylamine, triethylamine, triisoproplyamine, tripropylamine, imidazole, 1,5-diazabicylo[4.3.0]non-5-ene (DBN), 1,4-diazabicylo[2.2.2.] octane (Dabco™), 1,8-diazabicyclo[5.4.0]undec-7-ene (DBU). Preferred hindered bases are 2,4,6-collidine, 2.6-lutidine, N,N-diisopropylethylamine, N-ethlydicyclohexylamine, tripropylamine.

The number of molar equivalents of acid halide and hindered base used in a selective acylation reaction based on the moles of starting material can vary depending on the choice of acid halide and hindered base as well as other desired reaction parameters and conditions. In theory, it may be necessary to use only one equivalent of an acid halide to avoid bis- or higher order acylation products. However, excess acid halide is preferred to ensure complete reaction of the starting material with the greatest percent yield of end product and/or to increase the rate of reaction.

When using an excess of acid halide and/or hindered base, selectivity of the acylation should not be sacrificed or it should be within tolerable limits. Preferably greater than 2 equivalents, or greater than about 3 equivalents, of each of an acid halide and hindered base are used. More preferably, about 4 equivalents or more of each acid halide and hindered base are used. In certain embodiments, the number of equivalents of the acid halide is not equivalent to the number of equivalents of the hindered base. In a preferred embodiment, the number of equivalents of the acid halide is substantially similar to the number of equivalents of hindered base.

Regarding complete reaction of the starting material, for commercial applications, preferably less about 3%, or less than about 1%, of the starting material remains after the selective acylation reaction, and more preferably, less than about 0.1% remains. Further, with respect to generation of unwanted side products, preferably less than about 3%, or less than about 2%, of the bis- or higher order acylation product is formed, and more preferably less than about 1% is formed.

Without wishing to be bound to any particular theory, when the hindered base is a pyridine derivative, the reaction is believed to proceed through a positively charged acyl pyridinium reactive intermediate. Accordingly, if an excess of acid halide is used, an excess of the hindered base also should be used so that an excess of the acyl pyridinium intermediate is formed thereby facilitating the complete reaction of the starting material. If other hindered bases also proceed through reactive intermediates with an acid halide, then an excess of the hindered base should be used. However, because the reaction may proceed through an acyl/hindered base intermediate, it may be unnecessary to have greater than one equivalent of the hindered base present as only one equivalent of acid halide should be used up in the reaction with the starting material so that only one equivalent of the hindered base is necessary to scavenge the free halide. Regardless, the determination of an appropriate number of equivalents of acid halide and hindered base to use in a particular selective acylation reaction is considered to be within the level of skill in the art.

Other reaction parameters and conditions may depend on a variety of factors, e.g., the particular starting material, the spatial location and steric environment of the secondary hydroxyl groups to be selectively acylated, the spatial location and steric environment of other secondary hydroxyl groups, and the choice of hindered base and acid halide.

In one alternative embodiment, a suitable solvent may be aprotic, substantially anhydrous, and able to dissolve or solubilize the starting material(s) and acylating reagents to a sufficient degree so that a higher throughput of end product may be realized and excess amounts of solvents can be avoided. However, in all applications, each of these criteria may not be necessary. Preferably, the solvent can solubilize the starting material at least at a concentration of about 10% by weight or more, or about 15% by weight or more. More preferably, the solvent can solubilize the starting material at least at a concentration of about 20% by weight or more.

In addition, a suitable solvent should not react with the acylation reagents, i.e., the acid halide and the hindered base, or create any unwanted side products with the starting material. Accordingly, choice of a solvent depents on the choice of acid halide and hindered base, as well as the functionality present on the starting material. Ideally, the only reactive sites present on the starting material are the secondary hydroxyl groups, thereby minimizing the possibility of unwanted reactions elsewhere. Examples of solvents include, among others, acetone, acetonitrile ($CH_3CN$), 1,2-dimethoxyethane (mono-glyme), dimethylformamide (DMF), tetrahydrofuran (TBF), and toluene.

Other reaction conditions that may be varied include the time and temperature of the selective acylation reaction. In commercial embodiments, an increase of each of these parameters-increases the cost of the reaction, i.e., the cost of making the end product. Thus, minimizing the time and temperature of the reaction is desirable and may be achieved through the judicious choice of the above-discussed parameters.

For example, in a commercial process, a reaction time of less than about 8 hours is preferred (e.g. representing an employee shift), with reaction times of about 6 hours or about 4 hours more preferred. Regarding the temperature of reaction, the closer it is to about ambient temperature, the lower the amount of energy that needs to be used to either heat or cool the reaction thereby making the process more cost effective. Moreover, temperature sensitivity of the starting material and the end product should be taken into consideration when selecting the selective acylating reagents and other reaction parameters and conditions.

In addition, a selective acylation reaction may be carried out at ambient pressure in an atmospheric environment. Preferably the reaction is conducted in an inert atmosphere, e.g. nitrogen or argon. In addition, the reaction may be carried out at a pressure greater than or less than atmospheric pressure.

As with most chemical reactions, its progress may be monitored to completeness, e.g., using thin layer chromatography (TLC) or high performance liquid chromatography (HPLC). In some embodiments, a reaction may be deemed complete with about 90% of the end products is acylated at the desired hydroxyl group, e.g., at the C-2' position of a taxane molecule, and/or about 5% or less of the starting material is unreacted. In other embodiments, a reaction may be deemed complete when about 95% of the end products is acylated at the desired hydroxyl group and/or about 0.1% or less of the starting material is unreacted. Subsequent to completion of the selective acylation reaction or after a specific reaction time, work up of the acylation reaction, and isolation and purification of the selectively acylated end product may be accomplished using techniques readily known in the art.

For example, work up of selective acylation reaction conducted in $CH_3CN$ typically involves treating the reaction solution with a dilute hydrochloric acid (HCl) solution, partitioning with ethyl acetate (EtOAc), washing the organic layer with a dilute sodium bicarbonate ($NaHCO_3$) solution, washing the organic layer with a salt solution (brine), drying the organic layer with sodium sulfate ($Na_2SO_4$), and evaporating the organic layer to an amorphous solid. Subsequently, the amorphous solid may be crystallized using an appropriate solvent or solvent system.

Because use of excess acid halide and hindered base preferred, polymeric resins such as amino-functionalized resin beads or cation exchange resins may be used in the work up of reaction to facilitate removal of the excess acylation reagents. The polymeric resins typically are added to the reaction solution after completion of the reaction, then filtered out in the subsequent work up. Preferably an excess of the polymeric resin is used compared to the acylation reagent to be removed. For example, a quantity of polymeric resin that is about 2 equivalents, or about 4 equivalents is used. More preferably, about 6 equivalents or more of the polymeric resin is used. Removal of an acid halide, e.g., benzoyl chloride, may be realized by suing an amino-functionalized resin bead, e.g., Mitsubishi WA21J beads. Removal of a hindered base such as a pyridine derivative, e.g., 2,6-lutidine, may be achieved using a cationic exchange resin.

Alternatively, it was discovered that if the selective acylation reaction is conducted in THF with an acid chloride, much of the hydrochloric acid salt of the pyridine derivative formed during the course of the reaction may be removed by filtration. Although this may not be possible when $CH_3CN$ is the solvent as the hydrochloric acid salt of the pyridine derivative is soluble in $CH_3CN$. Subsequent precipitation of the crude end product in an excess of an appropriate solvent, e.g., hexane or heptane, was found to remove much of the remaining hindered base, the acid chloride, and any anhydride that formed during reaction.

The end product of the selective acylation reaction may be analyzed using analytical techniques known in the art such as infrared (IR) spectroscopy, nuclear magnetic resonance (NMR) spectroscopy, e.g., $^1H$-NMR and $^{13}C$-NMR, high performance liquid chromatography (HPLC), e.g., reversed phase HPLC, and/or mass spectrometry (MS), e.g., electrospray ionization MS (ES-MS) and matrix-assisted laser desorption ionization MS (MALDI-MS). A combination of these techniques also may be used, e.g., HPLC-MS.

In a preferred embodiment of the above-described methodology, the invention is directed to methods of selectively acylating a taxane molecule or mixtures of taxane molecules, e.g., from biomass or biomass extracts. Particularly, the method is directed to selectively acylating the hydroxyl group located at a C-2' position of a taxane molecule while the hydroxyl group located at the C-7 position of the taxane molecule remains unchanged. The method generally includes the steps of providing a solution comprising a taxane molecule in an organic solvent and contacting the solution with a hindered base and an acid halide whereby the hydroxyl group located at the C-2' position is selectively acylated. It should understood that the above description of the general selective acylation reaction, including reagents, reaction parameters and conditions, and other information, applies equally to the selective acylation of a taxane molecule.

In the synthesis of taxane molecules, or in the conversion of taxane molecules into other taxane molecules, it may be desirable to selectively acylate the C-2' hydroxyl group of the taxane molecule while maintaining the C-7 hydroxyl group unprotected. For example, to meet Good Manufacturing Practice (GMP) standards, paclitaxel from various sources can be selectively acylated with a benzoyl halide using methods of the invention to produce a semi-synthetic intermediate which can be transformed back into paclitaxel. Provided that substantially all the original paclitaxel was converted to the semi-synthetic intermediate, the resulting paclitaxel can be used in commercial pharmaceutical preparations. Thus, performing a selective acylation reaction where the C-7 hydroxyl group of a taxane molecule remains unprotected eliminates additional protection and deprotection steps, thereby reducing the overall steps necessary in the synthetic scheme and providing a more cost effective methodology.

A selective acylation reaction also may be conducted using a mixture of taxane molecules, each of which is selectively acylated at the desired hydroxyl group, e.g., the C-2' hydroxyl group. Mixtures of paclitaxel, cephalomannine, taxol C, and other taxane molecules occur in biomass or partial separations or extracts from biomass. According to methods of the invention, two or more of paclitaxel, cephalomannine, taxol C, and other taxane molecules may be selectively acylated together in one reaction. Thus, the methods of the invention permit selective acylation of multiple taxane molecules in one step. Subsequently, the selectively acylated mixture of taxane molecules may be converted to a particular taxane molecule determined by the choice of acid halide.

A preferred starting material is a taxane molecule having the formula:

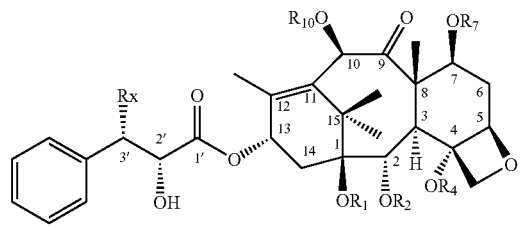

where each of $R_1$, $R_2$, $R_4$, $R_7$, and $R_{10}$ independently is hydrogen, an alkyl group, an acyl group, an aryl group, an arylalkyl group, a vinyl group, an ether group, an ester group, a glycoside group, an oxo-group, or a hydroxyl protecting group, provided that one of $R_2$, $R_7$ and $R_{10}$ is hydrogen. Preferably, $R_1$ is hydrogen; $R_2$ is an acyl group or a hydroxyl protecting group; $R_4$ is an acetate group; $R_7$ is hydrogen, an alkyl group, an aryl group, an ester group, an ether group, a glycoside group, an oxo-group, or a hydroxyl protecting group, and $R_{10}$ is hydrogen, an alkyl group, an aryl group, an ester group, ether group, or a hydroxyl protecting group; $R_{10}$ is hydrogen, an alkyl group, an aryl group, an ester group, an ether group, or a hydroxyl protecting group, provided that one of $R_2$, $R_7$ and $R_{10}$ is hydrogen. More preferably, $R_1$ is a hydrogen, $R_2$ is a benzoyl group (PHC(O)—), $R_4$ is an acetate group (CH$_3$C(O)—), $R_7$ is hydrogen, and $R_{10}$ is an acetate group; or $R_1$ is a hydrogen, $R_2$ is a benzoyl group (PhC(O)—), $R_4$ is an acetate group (CH$_3$C(O)—), $R_7$ is hydrogen, and $R_{10}$ is hydrogen.

As stated above, Rx can be an amino group, a salt of an amino group, an amino group that is protected with an amino protecting group, or a substituent which may be converted into an amino group. For example, Rx may be an iminio group having the formula:

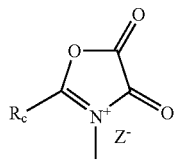

where RC is an alkyl group, an aryl group, an arylalkyl group, an vinyl group, an ether group, or a heterocyclic group; and Z is a counterion such as chlorine (Cl). While performing selective acylation, Rx is preferably an amino group that is protected as an amide (—NHC(O)—), an imine (—N=CH—), or a carbamate, (—NHC(O)O—).

More preferably, Rx is an imine group having the formula —N=CHRc, where Rc is an alkyl group, an aryl group, an arylalkyl group, an vinyl group, an ether group, or a heterocylic group; or Rx is an amide group having the formula —NHC(O)R$_N$, where R$_N$ is an alkyl group, an aryl group, an arylalkyl group, a vinyl group, an ether group, or a heterocylic group. Preferred Rc groups include, among others, aryl groups such as phenyl, alylalkyl groups such as benzyl, vinyl groups such as 1-methyl-1-propenyl (CH$_3$CH=C(CH$_3$)—), alkyl groups such as n-pentyl, propyl, 1-methyl-propyl (CH$_3$CH$_2$CH(CH$_3$)—), and heterocyclic groups such as 2-furanyl. Examples of R$_N$ groups include, among others, acetyl (CH$_3$C(O)—), HOC(O)—, (CH$_3$OC(O)—, (CH$_3$CH(OH)C(OH)(CH$_3$)—) and PhNHC(O)—. Preferred R$_N$ groups include, but are not limited to, phenyl, 1-methyl-1-propenyl, n-pentyl, propyl, 1-methyl-propyl, benzyl, and 2-furanyl as shown in Table 1.

A preferred end product of a selective acylation reaction with a taxane molecule is a taxane molecule having the formula:

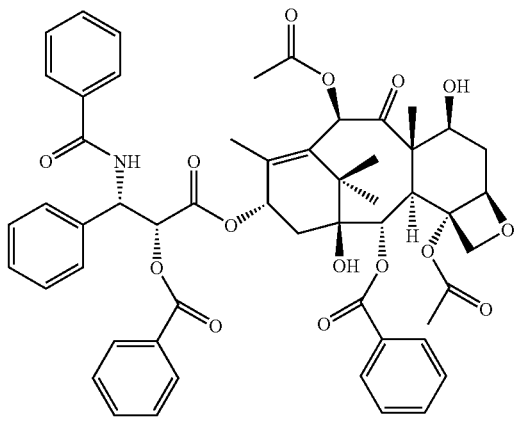

Another preferred end product of a selective acylation reaction with a taxane molecule is a taxane molecule having the formula:

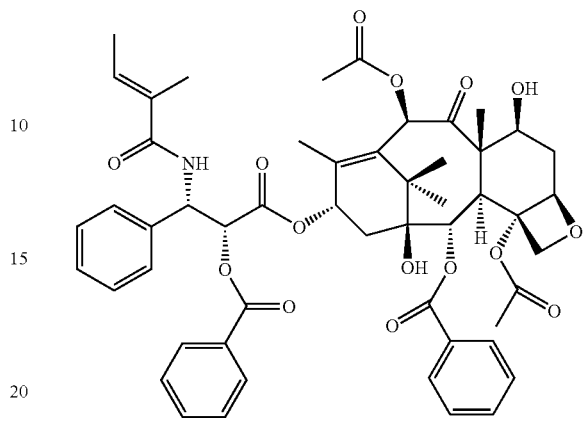

Other preferred end products are the known taxane molecules depicted in Table 1 with a benzoyl group attached to the 2'-oxygen.

Preferably at least about 85% of the end product taxane molecule is selectively acylated at the C-2' hydroxyl group without acylation at the C-7 hydroxyl group. Further, preferably less than about 1% of a bis- or higher order acylated compound is formed and/or less than about 0.1% of the starting taxane molecule(s) remain unreacted.

In the selective acylation of a taxane molecule, preferred acid halides are benzoyl chloride, tigloyl halide, hexanoyl chloride (caproyl chloride), butyryl chloride, 2-methylbu-tyryl chloride, phenylacetyl chloride, furoyl chloride, and tert-butyl chloroformate. Preferred hindered bases are tri-alkylamines having two of their alkyl groups larger than ethyl, and pyridine derivatives that are substituted at least at its 2- and 6-positions. Examples of preferred hindered bases are 2,4,6-collidine, 2,6-lutidine, NN-diisopropylethylamine, N-ethyldicyclohexylamine, and tripropylamine.

The quantity of each of the acid halide and hindered base is preferably about 4 or more equivalents based on the moles of starting taxane molecule(s), and more preferably about 5 or more equivalents. One preferred embodiment employs about 5 equivalents of benzoyl chloride and about 5.5 equivalents of 2,6-lutidine at about ambient temperature.

The preferred time of reaction is less than about 6 hours, and more preferably less than about 4 hours. The preferred temperature of the reaction is less than about 40° C. and more preferably about ambient temperature.

The preferred organic solvent for conducting a selective acylation reaction with a taxane molecule is THF. One reason for this choice is that THF will typically solubilize certain taxane molecules at a concentration of about 20% or greater. If THF is the organic solvent, the work up of the reaction is as described above. The preferred work up generally includes filtering the salt of the pyridine derivative and slowly adding the filtrate to about four or five times excess of hexane or heptane which causes the end product taxane molecule(s) to precipitate while the acylation reagents remain in solution. Heptane is the preferred anti-solvent. It should be understood that a larger excess of an anti-solvent may be used, e.g., a ten-fold excess.

Optionally, the resulting taxane mixture of the present invention may be purified using crystallization and/or one or more recrystallizations, depending on the desired purity of the end product taxane molecule. Crystallization and recrystallization is usually conducted using a binary or ternary solvent system, i.e., at least one solubilizing solvent and at least one anti-solvent. Examples of solubilizing solvents may include, among others, any halogenated hydrocarbon. Specific solvents may also include acetone, methyl tert-butyl ether, methylene chloride, trifluorotoluene, and THF, for example. Examples of anti-solvents, may include any hydrocarbon solvents such as, for example, hexane and heptane. Examples of other solvent systems useful with taxane molecules may include, among others, any halogenated hydrocarbon alone or combined with any hydrocarbon alkane, acetone/hexane, and methylene chloride/hexane. Methylene chloride/hexane is preferred.

The resulting aceylated taxane molecule may be converted into a taxane molecule in accordance with the processes described in U.S. Ser. No. 60/370,583, filed Apr. 5, 2002. This application is incorporated herein by reference in its entirety.

The invention is further illustrated by the following non-limiting examples.

EXAMPLES

Solvents and reagents were purchased from Sigma-Aldrich Co. (Milwaukee, Wis.). $^1$H NMR and $^{13}$C NMR chemical shifts are reported in parts per million (ppm) relative to tetramethylsilane.

Example 1

Selective Acylation of Paclitaxel with Benzoyl Chloride and 2.6-Lutidine or 2,4,6-Collidine A 25% (w/v) solution of paclitaxel in anhydrous tetrahydrofuran (THF) was prepared. 0.5 mL aliquots of this solution (0.148 mmol) were added to small vials, and treated with 5.5 equivalents of hindered base followed by 5.0 equivalents of benzoyl chloride. The reactions were stirred at room temperature for 4 hours and sampled for HPLC analysis using the HPLC protocol described below. The 2'-O-benzoyl paclitaxel (2'-OBz paclitaxel) was substantially identical to that reported by Kingston et al, in U.S. Pat. Nos. 5,319,112 and 5,470,866. The 2',7-bis-O-benzoyl paclitaxel (2',7-bis-OBz paclitaxel) was isolated and identified by $^1$H NMR and $^{13}$C NMR. Table 2 shows the percentages of starting material and major products as determined by HPLC analysis.

TABLE 2

| Base | % Paclitaxel | % 2'OBZ Paclitaxel | % 2',7-bis-OBZ Paclitaxel |
|---|---|---|---|
| 2,6-Lutidine | 0.43 | 99.44 | 0.12 |
| 2,4,6-Collidine | 0.52 | 99.31 | 0.17 |

HPLC Method: Column: Supelco Diphenyl, 150×4.6 mm, 5 micron. Flow Rate: 1.5 mL/min. Gradient: Start at 70%/30% water/acetonitrile (CH$_3$CN) with a linear gradient reaching 50%/50% water/CH$_3$CN at 10 minutes, then a linear gradient reaching 20%/80% water/CH$_3$CN at 13 minutes, then hold until 16 minutes. Re-equilibration is with 70%/30% water/CH$_3$CN for 4 minutes. Detection: 227 and 254 nm.

2',7-Bis-O-Benzoyl Paclitaxel NMR Results $^1$H NMR, 400 MHz (CDCl$_3$): 1.18 s 3H, 1.20 s 3H, 1.80 m 1H, 1.95 s 6H, 2.06 br s 3H, 2.15 m 1H, 2.37 m 1H, 2.45 s 3H, 2.79 m 1H, 4.05 d (6.8 Hz) 1H, 4.34 d (8.0Hz) 1H, 4.34 d (8.0Hz) 1H, 5.00 d (8.4 Hz) 1H, 5.73–5.80 m 3 H, 6.05 dd (3.6,8.8Hz) 1 H, 6.24 t (7.6 Hz) 1 H, 6.43 s 1H, 7.16 d (9.2 Hz) 1H, 7.31–8.13 m 25 H.

$^{13}$C NMR 100 MHz (CDCl$_3$): 11.04, 14.50, 20.36,21.33, 22.51, 26.35, 33.81, 35.42, 43.18, 46.58, 53.32, 56.15, 71.81, 72.02, 74.64, 74.73, 76.29, 78.79, 80.71, 83.96, 126.68, 127.02, 128.04, 128.52, 128.67, 128.68,129.05, 129.10, 129.73, 129.82, 130.13, 131.91, 132.66, 133.67, 133.72, 133.83, 136.86, 141.26, 156.75, 165.13, 165.48, 166.89, 167.14, 168.22, 168.24, 169.53, 202.52.

Example 2

Selective Acylation of Cephalomannine with Benzoyl Chloride and 2.6-Lutidine

A 25-mL flask was thoroughly dried with a heat gun and cooled by passing nitrogen through it. Cephalomannine (2.0 g, 2.41 mmol) was added, followed by anhydrous THF (10 mL). Within several minutes after stirring at room temperature, the solution was homogeneous. Next, 2,6-lutidine (1.6 ml, 5.5 eq.) was added at once and stirred for about 2 minutes. Benzoyl chloride (1.4 mL, 5.0 eq.) was added over 2-3 minutes. About 5 minutes after the addition of the acylation reagents was complete, the stirred solution became heterogeneous. HPLC assays were performed at various intervals and at about 4 hours, the reaction was deemed complete.

The 2,6-lutidine-HCl was filtered off through a sintered glass funnel and washed with about 5 mL of anhydrous THF. The combined filtrate was added to about 60 mL of heptane over about 5 minutes, causing precipitation. The suspension was transferred to a Buchner funnel and the collected yellow solid was washed three times with about 5 mL of a 4:1 heptane:THF solution. The yellow solid was then added to about 10 mL of methylene chloride (CH$_2$Cl$_2$) and stirred for about 10 minutes. Then, about 25 mL of heptane was added over about 10 minutes. After siring for about 10 minutes, the crystalline solid was filtered through a Buchner funnel and washed two times with about 5 mL of a 2.5:1 heptane: CH$_2$Cl$_2$ solution. After drying for about 2 days under vacuum at about 40–50° C., the crystalline solid weighed 2.06 grams and contained 2.00 g 2'-O-benzoyl cephalomannine (2'-OBz cephalomannine) (88.9% yield), 0.3% unreacted cephalomannine, and no detectable 2',7-bis-O-benzoyl cephalomannine as determined by HPLC.

2'-OBZ Cephalomannine NMR Results $^1$H NMR, 400 MHz (CDCl$_3$): 1.14 s 3H, 1.26 s 3H, 1.68 s 3H, 1.72 dd (1.2, 7.2 Hz) 3H, 1.82 br s3H, 1.87 m 1H, 1.95 d (1.2 Hz) 3H, 2.15 m 1H, 2.23 s 3H, 2.31 m 1H, 2.41 s 3H, 2.50 m 1H, 3.81 d (6.8 Hz) 1H, 4.18 d (8.4 Hz) 1H, 4.30 d (8.4 Hz) 1H, 4.45 dd (6.8, 9.6 Hz) 1H, 4.96 dd (2.0, 9.2 Hz) 1H, 5.62 d (4.0 Hz) 1H, 5.68 d (6.8 Hz) 1H, 5.90 dd (4.0, 8.8 Hz) 1 H, 6.26 t (7.6) 1H, 6.30 s 1H, 6.44 m 1H, 6.59 d (8.8 Hz) 1H, 7.30–8.12 m 15 H.

$^{13}$C NMR 100 MHz (CDCl$_3$): 9.58, 12.44, 13.98, 14.86, 20.81, 22.16, 22.61, 26.81, 35.48, 35.49, 43.15, 45.54, 52.75, 58.48, 71.80, 72.11, 74.73, 75.10, 75.59, 76.40, 79.27, 80.96, 84.43, 126.58, 128.39, 128.66, 128.70, 129.00, 129.13, 129.79, 130.18, 131.51, 131.70, 132.63, 133.66, 133.86, 137.19, 142.98, 165.58, 167.06, 168.14, 168.76, 169.77, 171.25, 203.83.

Example 3

Survey of Hindered Bases in the Selective Acylation of Paclitaxel with 2-Furoyl Chloride A 25% (w/v) solution of paclitaxel in anhydrous THF was prepared. 0.5 mL aliquots of this solution (0.148 millimoles) were added to small vials, and treated with 5.5 equivalents of a hindered base followed by 5.0 equivalents of 2-furoyl chloride. The reactions were stirred at room temperature for 4 hours, and sampled for HPLC analysis using the HPLC protocol described in Example 1. Table 3 shows the percentages of starting material and major products as determined by HPLC analysis.

TABLE 3

| Base | % Paclitaxel | % 2'-0-Furoyl Paclitaxel | % 2',7-bis-O-Furoyl Paclitaxel |
| --- | --- | --- | --- |
| 2,3-Lutidine | 0 | 86.43 | 13.57 |
| 2,4-Lutidine | 0.64 | 88.10 | 11.26 |
| 2,5-Lutidine | 0.15 | 84.55 | 15.30 |
| 2,6-Lutidine | 0.18 | 99.57 | 0.26 |
| 3,4-Lutidine | 0.23 | 1.95 | 97.82 |
| 3,5-Lutidine | 0 | 0.04 | 99.96 |
| 2,3,5-Collidine | 0.16 | 79.76 | 20.08 |
| 2,4,6-Collidine | 0.21 | 98.91 | 0.89 |
| Pyridine | 0 | 0.13 | 99.87 |
| 2-Phenyl Pyridine | 67.05 | 32.77 | 0.18 |
| N-Ethyldicyclohexylamine | 0 | 99.95 | 0.05 |
| N,N-Diisopropyl-isobutylamine | 39.00 | 60.78 | 0.23 |
| N,N-diisopropylethyl-amine | 0 | 99.88 | 0.16 |
| Triethylamine | 0 | 88.87 | 11.13 |
| Tripropylamine | 0 | 99.22 | 0.78 |
| Imidazole | 0.17 | 93.29 | 6.54 |
| Diazabicyclooctane (DABCO) | 0 | 91.00 | 9.00 |
| 4-(N,N-Dimethylamino)-pyridine (DMAP) | 0 | 0.18 | 99.92 |
| Diazabicycloundecane (DBU) | 20.37 | 69.84 | 9.79 |

Example 4

Selective Acylation of Mixed Taxanes at Large Scale

A 5-L flask was thoroughly dried with a heat gun and cooled by passing nitrogen through it. A taxane mixture containing 89.5% taxane molecules (consisting of 11.6% paclitaxel (taxol A), 21.4% cephalomannine (taxol B), 43.7% taxol C, 0.2% taxol D, 3.5% taxol E, 8.7% taxol F, and 0.4% taxol G) (753.2 g, ~0.88 mol) was added, followed by anhydrous THF (3.0 L). Within several minutes after stirring at room temperature, the solution was homogeneous. Next, 2,6-lutidine (565 mL, 5.5 eq.) was added at once and stirred for about 2 minutes. Benzoyl chloride (510 mL, 5.0 eq.) was added over about 10 minutes (no significant exotherm was experienced). About 1 minute after the addition of the acylation reagents was complete, the stirred solution became heterogeneous. HPLC assays were performed at various intervals and at about 6 hours, the reaction was deemed complete.

The 2,6-lutidine-HCl was filtered off through a sintered glass funnel and washed with about 500 mL of anhydrous ThF. One-half of the combined filtrate was added to about 12 L of heptane over about 15 minutes, causing precipitation. This precipitate was filtered using a Buchner funnel. The other half of the filtrate was processed likewise. The collected yellow solid was washed twice with a total of about 3.75 L of a 4:1 heptane: THF solution. The yellow solid was then added to about 3 L of $CH_2Cl_2$ and stirred for about 10 minutes to yield a crystalline solid. Then, 6 L of heptane was added over about 10 minutes with stirring. After stirring for about 30 minutes, the crystalline solid was filtered using a Buchner funnel and washed three times with a total of about 6 L of a 3:1 heptane:$CH_2Cl_2$ solution. After drying for about 60 hours under vacuum at about 40–50° C.; the crystalline solid weighed 728 grams and contained 645.9 g 2-O'-benzoyl taxane molecules (85.4% yield), and less than 0.5% unreacted taxane molecules and 2',7-bis-O-benzoyl taxane molecules as determined by HPLC.

INCORPORATION BY REFERENCE

The content of each of the patent and non-patent documents referred to herein is expressly incorporated herein by reference.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of selectively acylating a taxane molecule, the method comprising the steps of (a) providing a solution of tetrahydrofuran and a taxane molecule having the formula:

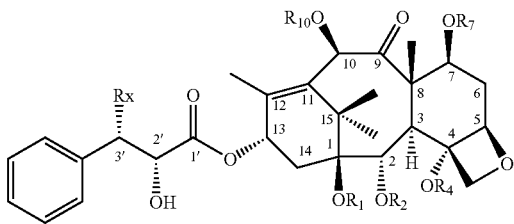

wherein
$R_1$ is hydrogen;
$R_2$ is a benzoyl group;
$R_4$ is an acetate group;
$R_7$ is hydrogen;
$R_{10}$ is hydrogen or an acetate group; and
Rx is N═CHRc or —NHC(O)$R_n$, wherein Rc is an alkyl group, an aryl group, an arylalkyl group, an vinyl group, or an ether group; and $R_n$ is an alkyl group, an aryl group, an arylalkyl group, a vinyl group, or an ether group; and (b) contacting the solution with a hindered base and an acylating agent thereby to selectively acylate the hydroxyl group located at the C-2' position, wherein the hindered base is selected from the group consisting of pyridine derivatives substituted at least at the 2-position, N,N-diisopropylisobutylamine, N-ethyldicyclohexylamine, triethylmntine, trilsopropylanilne, tripropylamine, iniidazole, 1,5-diazabicylo[4.3.0]non-5-ene, 1,4-diazabicyclo[2.2.2]octane, and 1,8-diazabicylo[5.4.0]undec-7-ene.

2. The method of claim 1, wherein the acylating agent is an acid halide.

3. The method of claim 2, wherein the acid halide is an acid chloride.

4. The method of claim 2, wherein the acid halide is selected from the group consisting of benzoyl halide, tigloyl halide, hexanoyl halide, butyryl halide, 2-methylbutyryl halide, phenylacetyl halide, furoyl balide, and tert-butyl halofonnate.

5. The method of claim 1, wherein the hindered base is a pyiidine derivative substituted at least at the 2-position.

6. The method of claim 4, wherein the hindered base is N-ethyldicyclohexylanune.

7. The method of claim 1, wherein the hindered base is selected from the group consisting of 2,6-lutidine and 2,4,6-collidine.

8. The method of claim 1 further comprising the step of crystallizing the acylated compound with at least one solubilizing solvent and optionally at least one antisolvent.

9. The method of claim 8, wherein the at least one solubilizing solvent is a halogenated hydrocarbon.

10. The method of claim 8, wherein the solubilizing solvent is selected form the group consisting of acetone, methyl tert butyl ether, trifluorotoluene, or THF.

11. The method of claim 8, wherein the solubilizing solvent is methylene chloride.

12. The method of claim 8, wherein the at least one solubilizing solvent is methylene chloride and the antisolvent is hexane.

13. The method of claim 8, wherein the antisolvent is a hydrocarbon alkane.

14. The method of claim 1 wherein $R_{10}$ is hydrogen.

15. The method of claim 1 wherein $R_{10}$ is an acetate group.

16. The method of claim 14 wherein Rx is N=CHRc, and Rc is selected from the group consisting of phenyl, 1-methyl-1-propenyl, n-pentyl, propyl, 1-methyl-propyl, benzyl; 2furanyl, and tert-butoxy.

17. The method of claim 14 wherein Rx is —NHC(O)$R_n$, and $R_n$ is selected from the group consisting of phenyl, 1-methyl-1-propenyl, n-pentyl, propyl, 1-methyl-propyl, benzyl, 2-Ibranyl, and tert-butoxy.

18. The method of claim 15 wherein Rx is N=CHR, and R is selected from the group consisting of phenyl, 1-methyl-1-propenyl, n-pentyl, propyl, 1-methyl-propyl, benzyl, 2-furanyl, and tert-butoxy.

19. The method of claim 15 wherein Rx is —NHC(O)$R_n$, and $R_n$ is selected from the group consisting of phenyl, 1-methyl-1-propenyl, n-pentyl, propyl, 1-methyl-propyl, beniyl, 2-furmnyl, and tert-butoxy.

20. A method of selectively acylating a taxane molecule, the method comprising the steps of
(a) providing a solution of tetrahydrofuran and a taxane molecule having the formula:

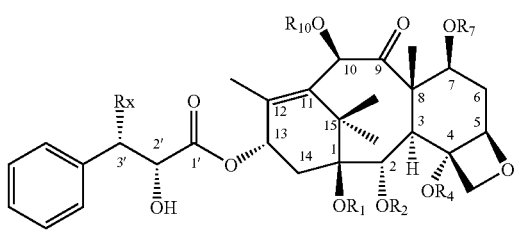

wherein
$R_1$ is hydrogen;
$R_2$ is a benzoyl group;
$R_4$ is an acetate group;
$R_7$ is hydrogen;
$R_{10}$ is hydrogen or an acetate group; and
Rx is N=CHRc or —NHC(O)$R_n$, wherein Rc is an alkyl group, an aryl group, an arylalkyl group, an vinyl group, or an ether group; and $R_n$ is an alkyl group, an aryl group, an arylalkyl group, a vinyl group, or an ether group; and
(b) adding 2,6-lutidine or N ethyldicyclohexylaniine and an acid chloride to the solution thereby to selectively acylate the hydroxyl group located at the C-2' position.

21. The method of claim 20 wherein $R_{10}$ is hydrogen.

22. The method of claim 20 wherein $R_{10}$ is an acetate group.

23. The method of claim 21 wherein Rx is N=CHRc, and Rc is selected from the group consisting of phenyl, 1-methyl-1-propenyl, n-pentyl, propyl, 1-methyl-propyl, benzyl; 2furanyl, and tert-butoxy.

24. The method of claim 21 wherein Rx is —NHC(O)$R_n$, and $R_n$ is selected from the group consisting of phenyl, 1-methyl-1-propenyl, n-pentyl, propyl, 1-methyl-propyl, benzyl, 2-furanyl, and tert(-butoxy.

25. The method of claim 22 wherein Rx is N=CHR, and R is selected from the group consisting of phenyl, 1-methyl-1-propenyl, n-pentyl, propyl, 1-methyl-propyl, beuzyl, 2furanyl, and tert-butoxy.

26. The method of claim 22 wherein Rx is —NHC(O)$R_n$, and $R_n$ is selected from the group consisting of phenyl, 1-methyl-1-propenyl, n-pentyl, propyl, 1-methyl-propyl, benzyl, 2-furanly, and tert-butoxy.

27. The method of claim 23 wherein the acid chloride is selected from the group consisting of benzoyl chloride, tigloyl chloride, hexanoyl chloride, butyryl chloride, 2-methylbutyryl chloride, phenylacetyl chloride, furoyl chloride, and tert butyl chioroformate.

28. The method of claim 24 wherein the acid chloride is selected from the group consisting of berazoyl chloride, tigloyl chloride, hexanoyl chloride, butyryl chloride, 2-methylbutyryl chloride, phenylacetyl chloride, furoyl chloride, and tert-butyl chloroformate.

29. The method of claim 25 wherein the acid chloride is selected from the group consisting of berazoyl chloride, tigloyl chloride, hexanoyl chloride, butyryl chloride, 2-methylbutyryl chloride, phenylacetyl chloride, furoyl chloride, and tert-butyl chloroformate.

30. The method of claim 26 wherein the acid chloride is selected from the group consisting of benzoyl chloride, tigloyl chloride, hexanoyl chloride, butyryl chloride, 2-methylbutyryl chloride, phenylacetyl chloride, furoyl chloride, and tert-butyl chioroformnate.

31. The method of claim 20 wherein $R_{10}$ is an acetate group, Rx is —NHC(O)$R_n$, wherein $R_n$ is phenyl, and the acid chloride is benzoyl chloride.

32. The method of claim 20 wherein $R_{10}$ is an acetate group, Rx is —NHC(O)$R_n$, wherein $R_n$ is 1-methyl-1-propenyl, and the acid chloride is benzoyl chloride.

33. The method of claim 20 wherein $R_{10}$ is an acetate group, Rx is —NHC(O)$R_n$, wherein $R_n$ is n-pentyl, and the acid chloride is benzoyl chloride.

34. The method of claim 20 further comprising the step of crystallizing the acylated compound with at least one solubilizing solvent and optionally at least one antisolvent.

35. The method of claim 34, wherein the at least one solubilizing solvent is a halogenated hydrocarbon.

36. The method of claim 34, wherein the solubilizing solvent is selected form the group consisting of acetone, methyl tert butyl ether, trifluorotoluene, or THF.

37. The method of claim 34, wherein the solubilizing solvent is methylene chloride.

38. The method of claim 34, wherein the at least one solubilizing solvent is methylene chloride and the antisolvent is hexane.

39. The method of claim 34, wherein the antisolvent is a hydrocarbon alkane.

40. The method of claim 1, wherein the method results in at least about 95% of an ending taxane acylated at the C-2' position and less than about 0.1% of the starting texans remains unreacted after the contacting step.

41. The method of claim 40, wherein the method results in at least about 99% of an ending taxane acylated at the C-2' position.

42. The method of claim 20, wherein the method results in at least about 95% of an ending taxane acylated at the C-2' position and less than about 0.1% of the starting taxane remains unreacted after the contacting step.

43. The method of claim 42, wherein the method results in at least about 99% of an ending taxane acylated at the C-2' position.

* * * * *

UNITED STATES PATENT AND TRADEMARK OFFICE
CERTIFICATE OF CORRECTION

PATENT NO. : 7,176,325 B2
APPLICATION NO. : 10/510063
DATED : February 13, 2007
INVENTOR(S) : Johnson et al.

It is certified that error appears in the above-identified patent and that said Letters Patent is hereby corrected as shown below:

Column 7,

Line 32: "(DBI)" should read --(DBU)--

Column 24,

Line 64: "triethylmntine" should read --triethylamine--

Line 64: "trilsopropylanilne" should read --triisopropylamine--

Column 24,

Line 65: "iniidazole" should read --imidazole--

Column 25,

Line 8: "balide" should read --halide--

Line 9: "halofonnate" should read --haloformate--

Line 11: "pyiidine" should read --puridine--

Line 43: "2-Ibranyl" should read --2-furanyl-

Line 51: "2-furmnyl" should read --2-furanyl--

Column 26,

Line 26: "tert(-butoxy" should read --tert-butoxy--

Line 39: "chioroformate" should read --chloroformate--

Line 41: "berazoyl" should read --benzoyl--

Line 54: "chioroformnate" should read --chloroformate--

UNITED STATES PATENT AND TRADEMARK OFFICE
CERTIFICATE OF CORRECTION

PATENT NO. : 7,176,325 B2
APPLICATION NO. : 10/510063
DATED : February 13, 2007
INVENTOR(S) : Johnson et al.

It is certified that error appears in the above-identified patent and that said Letters Patent is hereby corrected as shown below:

Column 28,

Line 1: "texans" should read --taxane--

Signed and Sealed this

Twenty-sixth Day of June, 2007

JON W. DUDAS
*Director of the United States Patent and Trademark Office*